United States Patent
Lu et al.

(10) Patent No.: US 9,650,685 B2
(45) Date of Patent: *May 16, 2017

(54) SELECTIVE DETECTION OF HUMAN RHINOVIRUS

(71) Applicant: The United States of America, as represented by the Secretary, Department of Health and Human Services, Washington, DC (US)

(72) Inventors: Xiaoyan Lu, Atlanta, GA (US); Dean D. Erdman, Decatur, GA (US)

(73) Assignee: The United States of America, as represented by the Secretary, Department of Health and Human Services, Rockville, MD (US)

( * ) Notice: Subject to any disclaimer, the term of this patent is extended or adjusted under 35 U.S.C. 154(b) by 171 days.

This patent is subject to a terminal disclaimer.

(21) Appl. No.: 14/570,569

(22) Filed: Dec. 15, 2014

(65) Prior Publication Data

US 2015/0099263 A1 Apr. 9, 2015

Related U.S. Application Data

(62) Division of application No. 12/315,758, filed on Dec. 5, 2008.

(51) Int. Cl.
*C12Q 1/68* (2006.01)
*C12P 19/34* (2006.01)
*C12Q 1/70* (2006.01)

(52) U.S. Cl.
CPC ....... *C12Q 1/701* (2013.01); *C12Q 2600/158* (2013.01)

(58) Field of Classification Search
None
See application file for complete search history.

(56) References Cited

U.S. PATENT DOCUMENTS

| 6,818,397 | B1 | 11/2004 | Lee et al. |
| 7,220,549 | B2 | 5/2007 | Buzby |
| 8,986,933 | B2 * | 3/2015 | Lu .......................... C12Q 1/701 435/6.1 |
| 2006/0008810 | A1 | 1/2006 | Lee et al. |
| 2007/0092871 | A1 | 4/2007 | Lodes et al. |

OTHER PUBLICATIONS

Bellau-Pujol et al., "Development of three multiplex RT-PCR assays for the detection of 12 respiratory RNA viruses," Journal of Virological Methods, 2005, vol. 126, pp. 53-63.*
Kares et al., "Real-time PCR for rapid diagnosis of entero- and rhinovirus infections using LightCycler," Journal of Clinical Virology, 2004, vol. 29, pp. 99-104.*
Fadlalla, K. et al., "*Ruta graveolens* Extract Induces DNA Damage Pathways and Blocks Akt Activation to Inhibit Cancer Cell Proliferation and Survival," *Anticancer Research* 31: 233-242 (2011).
Massung, Robert F., "Nested PCR Assay for Detection of Granulocytic Ehrilichiae," *J. Clin. Microbiol.* 1998, 36(4): 1090-1095.
ViraCor Laboratories, "Rhinovirus", www.viracor.com, Jul. 21, 2009.
Applied Biosystems, "Real-Time PCR-Based Assay," https://products.appliedbiosystems.com (Jun. 23, 2009).
Eppendorf website, http://www.eppendorf.com (Jun. 16, 2009).

* cited by examiner

*Primary Examiner* — Young J Kim
(74) *Attorney, Agent, or Firm* — Dinsmore & Shohl LLP

(57) ABSTRACT

A process for detecting human rhinovirus nucleic acid in a biological sample, includes producing an amplification product by amplifying an human bocavirus nucleotide sequence using a forward primer of SEQ ID NO: 1, and a reverse primer of SEQ ID NO: 2, and measuring said amplification product to detect human rhinovirus in said biological sample. Also provided are reagents and methods for detecting and distinguishing human rhinovirus from other viruses. A kit is provided for detecting and quantifying human rhinovirus in a biological sample.

9 Claims, 3 Drawing Sheets

Figure 1

COORELATION COEFFICIENT: 0.999  SLOPE: -3.678  INTERCEPT: 41.798  Y= -3.678 X + 41.798
PCR EFFICIENTCY: 87.0 %

SELECTIVE DETECTION OF HUMAN RHINOVIRUS

CROSS REFERENCE TO RELATED APPLICATIONS

This application is a divisional of U.S. patent application Ser. No. 12/315,758filed Dec. 5, 2008, and claims priority thereto.

GOVERNMENT INTEREST

The invention described herein may be manufactured, used, and licensed by or for the United States Government.

FIELD OF THE INVENTION

This invention relates generally to processes for detection of virus in fluid samples. More specifically, the instant invention relates to selective detection of human rhinovirus (HRV) in biological or other fluid media. Processes are described for rapid and sensitive detection of HRV in human and animal biological samples and quantification thereof Diagnostic kits are provided for detection of HRV in a clinical, laboratory, or field setting.

BACKGROUND OF THE INVENTION

Human rhinovirus (HRV) infections are among the most frequent cause of the common cold. (Pitkaranta, A., and F. G. Hayden. 1998. *Ann. Med.* 30:529-537). Recently HRVs have been linked to severe lower respiratory illnesses in young children (Miller E. K., 2007. *J. Infect. Dis.* 195:773-781, Monto A. S., Clin. Ther. 2001; 23:1615-1627), the elderly (Hicks, L. A., *J. Am. Geriatr. Soc.*, 2006; 54:284-289, Nicholson, K. G., *Br. Med. J.*, 1996; 313:1119-1123, Wald, T., *Ann. Intern. Med.*, 1995; 123:588-593) and the immunocompromised (Gosh, S. R., *Clin. Infect. Dis.*, 1999; 29:528-532, Ison, M. G., *Clin. Infect. Dis.*, 2003; 36:1139-1143). Persons with underlying respiratory disease, like asthma, chronic bronchitis and cystic fibrosis may also have increased risk of severe HRV-associated complications. (Friedlander, S. L., and W. W. Busse, *J. Allergy. Clin. Immunol.*, 2005; 116:267-273; Khetsuriani, N, *J. Allergy. Clin. Immunol.*, 2007; 119:314-321; Smyth, A. R., *Arch. Dis. Child.*, 1995; 73:117-120).

The family Picornaviridae contains HRVs together with the human enteroviruses (HEVs) (King, A. M., et al. 2000. Picornaviridae, p. 657-678. In Virus Taxonomy. Seventh Report of the International Committee for the Taxonomy of Viruses. Academic Press, San Diego, Calif.). At least 100 distinct HRV serotypes of this family are assigned to two phylogenetic groups, A and B (Andries, K., *J. Virol.*, 1990; 64:1117-1123), and new genetic variants of HRV have recently been reported. (Lamson, D., *J. Infect. Dis.*, 2006; 194:1398-1402; McErlean, P., *J. Clin. Virol.*, 2007; 39:67-75.)

Clinically, presentation of HRV infection is of little diagnostic value due to symptomatic similarity with numerous other infectious agents. Compounding problems with HRV identification, laboratory diagnosis suffers from the failure of some strains to grow in cell culture and by their extreme antigenic variability, precluding routine use of antigen detection methods or serology. (Lu, X., *J. Clin. Microbiol.* 2008; 46(2):533-9.) HRV identification with prior art methods is difficult, and distinguishing HRVs from HEVs in the same clinical sample using acid liability is ineffective for many strains. Thus, modern efforts have attempted to use reverse-transcription polymerase chain reaction (RT-PCR) assays to increase the detection sensitivity and differentiation of HRVs from co-existing infectious agents.

Nucleic acid assays for HRV typically target the 5'-noncoding region (5'NCR) of the viral genome. The 5'NCR is preferred due to the availability of highly conserved sequences that support the complex secondary structures of the HRV/HEV internal ribosome entry site (Witwer, C., *Nucleic. Acids Res.*, 2001; 29:5079-5089). Whereas the locations of these conserved sequences offer considerable flexibility for designing targeted primer/probes for HEV real-time RT-PCR assays (Kares, S., *J. Clin. Virol.*, 2004; 29:99-104, Nijhuis, M., *J. Clin. Microbiol.*, 2002; 40:3666-3670; Verstrepen, W. A., *J. Clin. Microbiol.*; 2001; 39:4093-4096), development of comparable assays for HRVs is hampered by their greater genetic variability and the paucity of published HRV sequence data from the 5'-NCR. In addition, prior art nucleic acid assays require post-amplification processing of the amplicon by gel electrophoresis, probe hybridization, sequencing or restriction analysis to confirm and differentiate HRVs from HEVs (Andeweg, A. C., *J. Clin. Microbiol.*, 1999; 37:524-530; Atmar, R. L., and Georghiou, *J. Clin. Microbiol.*, 1993; 31:2544-2546; Billaud, G., *J. Virol. Methods*, 2003; 108:223-228; Blomqvist, S., *J. Clin. Microbiol.*, 1999; 37:2813-2816; Halonen, P., *J. Clin. Microbiol.*, 1995; 33:648-653; Kammerer, U., *J. Clin. Microbial.*, 1994; 32:285-291; Loens, K., *J. Clin. Microbiol.*, 2006; 44:166-171; Miller, E. K., *J. Infect. Dis.*, 2007; 195:773-781; Papadopoulos, N. G., *J. Virol. Methods*, 1999; 80:179-85).

More recently, real-time RT-PCR assays have been described for HRV/HEVs (Dagher, H., *J. Virol. Methods.*, 2004; 117:113-121; Deffernez, C., *J. Clin. Microbiol.*, 2004; 42:3212-3218; Kares, S., *J. Clin. Virol.*, 2004; 29:99-104, Nijhuis, M., *J. Clin. Microbiol.*, 2002; 40:3666-3670; Scheltinga, S. A., *J. Clin. Virol.*, 2005; 33:306-311). These assays did not detect all known HRV serotypes (Dagher, H., *J. Virol. Methods.*, 2004; 117:113-121; Deffernez, C., *J. Clin. Microbiol.*, 2004; 42:3212-3218; Scheltinga, S. A., *J. Clin. Virol.*, 2005; 33:306-311; Wright, P. F., *J. Clin. Microbiol.*, 2007; 45:2126-2129) or used difficult to interpret SYBR Green detection (Dagher, H., *J. Virol. Methods.*, 2004; 117:113-121; Wittwer, C T., *Biotechniques*, 1997; 22:130-131, 134-138). Moreover, these prior art assays are inaccurate due to the extensive genetic variability of the HRVs and lack of available sequence data in the public domain. Thus, no real-time RT-PCR assays specifically identify all HRVs relative to HEVs or other viral fluid components (Dagher, H., *J. Virol. Methods.*, 2004; 117:113-121; Deffernez, C., *J. Clin. Microbiol.*, 2004; 42:3212-3218, Scheltinga, S. A., *J. Clin. Virol.*, 2005; 33:306-311; Wright, P. F., *J Clin. Microbiol.*, 2007; 45:2126-2129). Finally, no prior art assay has successfully detected viral prototype strains. Thus, there is a need for a rapid, sensitive, and discriminatory assay for detection of HRV in complex clinical or laboratory samples in the presence or absence of other viral agents.

SUMMARY OF THE INVENTION

A process for detecting human rhinovirus in a biological sample includes producing an amplification product by amplifying a human rhinovirus nucleotide sequence using a forward primer homologous to a region within nucleotides 356-563 of human rhinovirus and a reverse primer homologous to a region within nucleotides 356-563 of human rhinovirus and measuring the amplification product under conditions for a polymerase chain reaction to detect human rhinovirus in the biological sample. The forward primer is illustratively of SEQ ID NO: 1 and the reverse primer is illustratively of SEQ ID NO: 2. Measuring the amplification product may illustratively be by using a probe complementary to a sequence of human rhinovirus. The probe may illustratively be of SEQ ID NO: 3. The inventive process is operable for detection of human rhinovirus infection in a biological sample.

The inventive process detects a first, second, or third detection signal by a variety of techniques such as liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, real-time RT-PCR, RT-PCR, nucleotide sequencing, or combinations thereof.

The inventive process allows for diagnoses human rhinovirus infection in a human subject. By comparing the first detection signal to a second detection signal, where the second detection signal results from the hybridization of a probe complementary to a sequence from a human rhinovirus.

A second detection signal is optionally obtained by detection within the same or a parallel biological sample possibly containing human enterovirus, polio virus, respiratory syncytial virus, human metapneumovirus, human parainfluenza viruses 1-4, adenovirus, coronaviruses 229E and OC43, influenza viruses A and B, and human bocavirus, and the hybridization of a probe complementary to a sequence from one or more viruses of said group.

An inventive process optionally also or independently detects the presence of human enterovirus in a biological sample that illustratively includes producing an amplification product by amplifying a human enterovirus nucleotide sequence using a forward primer homologous to a region within 356-563 of human enterovirus and a reverse primer homologous to a region within 356-563 of human enterovirus and measuring the amplification product under conditions for a polymerase chain reaction to detect human enterovirus in the biological sample A process is provided in which the second detection signal is generated in parallel with, prior to, or following the first detection signal. The complementary amplification product is illustratively generated by PCR amplification of a purified and titered human rhinovirus solution. The first detection signal is also optionally compared to a third detection signal from a nucleic acid calibrator extracted in parallel to the biological sample to provide further quantification data, with nucleic acid calibrator containing a known amount of human rhinovirus and a known amount of a medium similar to the biological sample.

A kit for detecting human rhinovirus infection is provided that includes a forward primer with sequence SEQ ID NO: 1, a reverse primer with SEQ ID NO: 2, and a non-degenerate probe. An exemplary non-degenerate probe has the sequence SEQ ID NO: 3.

Also provided is a nucleotide sequence of SEQ ID NO: 1, SEQ ID NO: 2, or SEQ ID NO: 3.

BRIEF DESCRIPTION OF THE DRAWINGS

FIG. 1 represents an alignment of partial 5'NCR sequences of 100 HRV and 52 HEV serotypes in regions corresponding to primers (SEQ ID NOS: 1 and 2 derived from to SEQ ID NOS: 12 and 14 respectively) and probe (SEQ ID NO. 3 derived from SEQ ID NO: 13) used for the inventive HRV real-time RT-PCR assay;

DETAILED DESCRIPTION OF THE PREFERRED EMBODIMENTS

Figure 2:
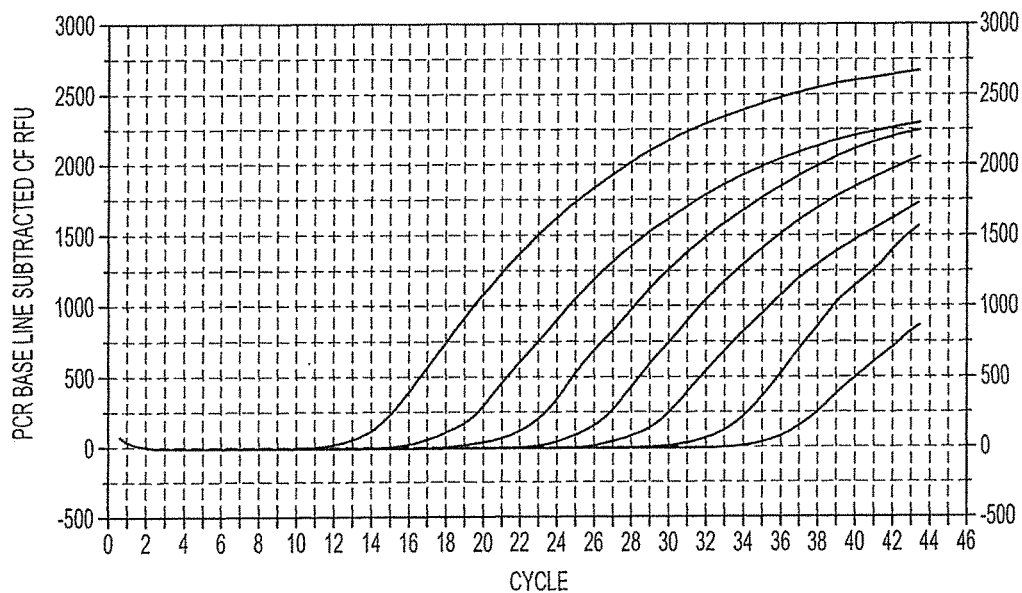
FIG. 2 represents a representative inventive real-time RT-PCR amplification plot obtained with serial 10-fold dilutions ($5\times10^1$ to $5\times10^7$ copies per reaction) of HRV14 RNA transcript demonstrating sensitivity and robustness of the inventive assay.
Figure 2:
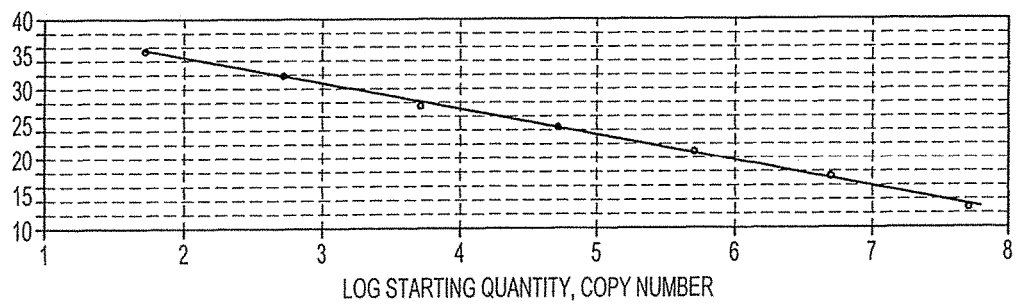

The high genetic variability of HRV and the presence of numerous other potential infectious agents capable of producing similar clinical symptoms highlights the need for a rapid, sensitive, and discriminatory assay and reagents for the detection and quantification of HRV in a fluid sample. The instant invention has utility for detection of HRV in biological samples, diagnosis of disease associated therewith, and discrimination against other viral pathogens such as HEV.

Several details of the current invention were published by Lu, X., *J Clin. Microbiol.* 2008; 46(2):533-9, the entire contents of which are incorporated herein by reference as if the entire text and figures are expressly set out herein.

The following definitional terms are used throughout the specification without regard to placement relative to these terms.

As used herein, the term "variant" defines either a naturally occurring genetic mutant of HRV or a recombinantly prepared variation of HRV, each of which contain one or more mutations in its genome compared to the HRV of HRV1B (accession no. D00239). The term "variant" may also refer to either a naturally occurring variation of a given peptide or a recombinantly prepared variation of a given peptide or protein in which one or more amino acid residues have been modified by amino acid substitution, addition, or deletion.

As used herein, the term "analog" in the context of a non-proteinaceous analog defines a second organic or inorganic molecule that possesses a similar or identical function as a first organic or inorganic molecule and is structurally similar to the first organic or inorganic molecule.

As used herein, the term "derivative" in the context of a non-proteinaceous derivative defines a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated. A derivative also defined as a degenerate base mimicking a C/T mix such as that from Glen Research Corporation, Sterling, Va., illustratively LNA-dA or LNA-dT, or other nucleotide modification known in the art or otherwise.

As used herein, the term "mutant" defines the presence of mutations in the nucleotide sequence of an organism as compared to a wild-type organism.

A "purified" nucleic acid molecule is one that is separated from other nucleic acid molecules that are present in the natural source of the nucleic acid molecule and is often substantially free of other cellular material, or culture medium when produced by recombinant techniques, or substantially free of chemical precursors or other chemicals when chemically synthesized. This term is exclusive of a nucleic acid that is a member of a library that has not been purified away from other library clones containing other nucleic acid molecules.

As used herein, the term "hybridizes under stringent conditions" describes conditions for hybridization and washing under which nucleotide sequences having at least 30%, 35%, 40%, 45%, 50%, 55%, 60%, 65%, 70%, 75%, 80%, 85%, 90%, or 95% identity to each other typically remain hybridized to each other. Such hybridization conditions are described in, for example but not limited to, Current Protocols in Molecular Biology, John Wiley & Sons, N.Y. (1989), 6.3.1 6.3.6; Basic Methods in Molecular Biology, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art. A preferred, non-limiting example of stringent hybridization conditions is hybridization in 6x sodium chloride/sodium citrate (SSC), 0.5% SDS at about 68° C. followed by one or more washes in 2×SSC, 0.5% SDS at room temperature. Another preferred, nonlimiting example of stringent hybridization conditions is hybridization in 6×SSC at about 45° C. followed by one or more washes in 0.2×SSC, 0.1% SDS at 50 to 65° C.

An "isolated" or "purified" nucleotide or oligonucleotide sequence is substantially free of cellular material or other contaminating proteins from the cell or tissue source from which the nucleotide is derived, or is substantially free of chemical precursors or other chemicals when chemically synthesized. The language "substantially free of cellular material" includes preparations of a nucleotide/oligonucleotide in which the nucleotide/oligonucleotide is separated from cellular components of the cells from which it is isolated or produced. Thus, a nucleotide/oligonucleotide that is substantially free of cellular material includes preparations of the nucleotide having less than about 30%, 20%, 10%, 5%, 2.5%, or 1% (by dry weight) of contaminating material. When nucleotide/oligonucleotide is produced by chemical synthesis, it is preferably substantially free of chemical precursors or other chemicals, i.e., it is separated from chemical precursors or other chemicals which are involved in the synthesis of the protein. Accordingly, such preparations of the nucleotide/oligonucleotide have less than about 30%, 20%, 10%, 5% (by dry weight) of chemical precursors or compounds other than the nucleotide/oligonucleotide of interest. In a preferred embodiment of the present invention, the nucleotide/oligonucleotide are isolated or purified.

As used herein, the term "isolated" virus or virus-like particle (VLP) is one which is separated from other organisms which are present in the natural source of the virus, e.g., biological material such as cells, blood, serum, plasma, saliva, urine, stool, sputum, nasopharyngeal aspirates, and so forth. The isolated virus or VLP can be used to infect a subject cell.

As used herein, the term "biological sample" is defined as sample obtained from a biological organism, a tissue, cell, cell culture medium, or any medium suitable for mimicking biological conditions, or from the environment. Non-limiting examples include, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions, throat or nasal materials. In a preferred embodiment, viral agents are contained in serum, whole blood, nasopharyngeal fluid, throat fluid, other respiratory fluid.

As used herein, the term "medium" refers to any liquid or fluid biological sample in the presence or absence of virus. Non-limiting examples include buffered saline solution, cell culture medium, acetonitrile, trifluoroacetic acid, combinations thereof, or any other fluid recognized in the art as suitable for combination with virus or cells, or for dilution of a biological sample or amplification product for analysis.

To determine the percent identity of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, nonlimiting example of a mathematical algorithm utilized for the comparison of two sequences is the algorithm of Karlin and Altschul, 1990, *PNAS* 87:2264 2268, modified as in Karlin and Altschul, 1993, *PNAS*. 90:5873 5877. Such an algorithm is incorporated into the NBLAST and XBLAST programs of Altschul et al., 1990, *J. Mol. Biol.* 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, *Nucleic Acids Res.* 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non-limiting example of a mathematical algorithm utilized for the comparison of sequences is the algorithm of Myers and Miller, 1988, *CABIOS* 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

As used herein, the terms "subject" and "patient" are synonymous and refer to a human or non-human animal, preferably a mammal including a human, non-primate such as cows, pigs, horses, goats, sheep, cats, dogs, avian species and rodents; and a non-human primate such as monkeys, chimpanzees, and apes; and a human, also denoted specifically as a "human subject".

The instant inventive process provides a rapid, specific, and sensitive assay process for detection of HRV in biological samples by amplifying one or more nucleotide sequences with greater specificity to strains of HRV than HEV or other viral agents and are present in a biological sample by processes similar to the polymerase chain reaction (PCR).

An oligonucleotide forward primer with a nucleotide sequence complementary to a unique sequence in an HRV nucleotide sequence illustratively in the 5'-NCR is hybridized to its complementary sequence and extended. Similarly, a reverse oligonucleotide primer complementary to a second strand of HRV DNA in the same or an alternate HRV region is hybridized and extended. This system allows for amplification of specific gene sequences and is suitable for simultaneous or sequential detection systems.

The present invention relates to the use of the sequence information of HRV for diagnostic process. In particular, the present invention provides a process for detecting the presence or absence of nucleic acid molecules of HRV, natural or artificial variants, analogs, or derivatives thereof, in a biological sample. The process involves obtaining a biological sample from various sources and contacting the sample with a compound or an agent capable of detecting a nucleic acid sequence of HRV, natural or artificial variants, analogs, or derivatives thereof, such that the presence of HRV, natural or artificial variants, analogs, or derivatives thereof, is detected in the sample. In a preferred specific embodiment, the presence of HRV, natural or artificial variants, analogs, or derivatives thereof, is detected in the sample by a reverse transcription polymerase chain reaction (RT-PCR) using the primers that are constructed based on a partial nucleotide sequence of the HRV virus. In a non-limiting specific embodiment, preferred forward primer to be used in a RT-PCR process is 5'-CPXGCCZGCGTGGY-3' (SEQ ID NO: 1) where P=pyrimidine derivative, a degenerate base mimicking a C/T mix (Glen Research Corporation, Archive Report 8.1), X=LNA-dA, Z=LNA-dT (Glen Research Corporation, Archive Report 20.1, Y=C or T, and a reverse primer 5'-GAAACACGGACACCCAAAGTA-3' (SEQ ID NO: 2). LNA denotes a locked nucleic acid and X includes a deoxyadenosine or deoxythymidine bonded thereto. LNAs were first detailed in Koshkin et al., *Tetrahedron* 54, 3607-3630 (1998). In preferred embodiments, the primers comprise the nucleic acid sequence of SEQ ID NOS: 1 and 2. A preferred agent for detecting HRV nucleic acid sequences is a labeled nucleic acid probe capable of hybridizing thereto. In a preferred embodiment, the nucleic acid probe is a nucleic acid molecule comprising or consisting of the nucleic acid sequence of 5'-TCCTCCGGCCCCTGAATGYGGC-3' (SEQ ID NO: 3), which sufficiently specifically hybridizes under stringent conditions to an HRV nucleic acid sequence when Y is C or T.

The process of the present invention can involve a real-time quantitative PCR assay. In a preferred embodiment, the quantitative PCR used in the present invention is TaqMan assay (Holland et al., *PNAS* 88(16):7276 (1991)). It is appreciated that the current invention is amenable to performance on other RT-PCR systems and protocols that use alternative reagents illustratively including, but not limited to Molecular Beacons probes, Scorpion probes, multiple reporters for multiplex PCR, combinations thereof, or other DNA detection systems.

The assays are performed on an instrument designed to perform such assays, for example those available from Applied Biosystems (Foster City, Calif.). In more preferred specific embodiments, the present invention provides a real-time quantitative PCR assay to detect the presence of HRV, natural or artificial variants, analogs, or derivatives thereof, in a biological sample by subjecting the HRV nucleic acid from the sample to PCR reactions using specific primers, and detecting the amplified product using a probe. In preferred embodiments, the probe is a TaqMan probe which consists of an oligonucleotide with a 5'-reporter dye and a 3'-quencher dye.

A fluorescent reporter dye, such as FAM dye (illustratively 6-carboxyfluorescein), is covalently linked to the 5' end of the oligonucleotide probe. Other dyes illustratively include such TAMRA, AlexaFluor dyes such as AlexaFluor 495 or 590, Cascade Blue, Marina Blue, Pacific Blue, Oregon Green, Rhodamine, Fluoroscein, TET, HEX, Cy5, Cy3, and Tetramethylrhodamine. Each of the reporters is quenched by a dye at the 3' end or other non-fluorescent quencher. Quenching molecules are suitably matched to the fluorescence maximum of the dye. Any suitable fluorescent probe for use in real-time PCR (RT-PCR) detection systems is illustratively operable in the instant invention. Similarly, any quenching molecule for use in RT-PCR systems is illustratively operable. In a preferred embodiment a 6-carboxyfluorescein reporter dye is present at the 5'-end and matched to Black Hole Quencher (BHQ1, Biosearch Technologies, Inc., Novato, Calif.). The fluorescence signals from these reactions are captured at the end of extension steps as PCR product is generated over a range of the thermal cycles, thereby allowing the quantitative determination of the viral load in the sample based on an amplification plot.

The HRV virus nucleic acid sequences are optionally amplified before being detected. The term "amplified" defines the process of making multiple copies of the nucleic acid from a single or lower copy number of nucleic acid sequence molecule. The amplification of nucleic acid sequences is carried out in vitro by biochemical processes known to those of skill in the art. The amplification agent may be any compound or system that will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, AmpliTaq Gold DNA Polymerase from Applied Biosystems, other available DNA polymerases, reverse transcriptase (preferably iScript RNase H+ reverse transcriptase), ligase, and other enzymes, including heat-stable enzymes (i.e., those enzymes that perform primer extension after being subjected to temperatures sufficiently elevated to cause denaturation). In a preferred embodiment, the enzyme is hot-start iTaq DNA polymerase from Bio-rad (Hercules, Calif.). Suitable enzymes will facilitate combination of the nucleotides in the proper manner to form the primer extension products that are complementary to each mutant nucleotide strand. Generally, the synthesis is initiated at the 3'-end of each primer and proceed in the 5'-direction along the template strand, until synthesis terminates, producing molecules of different lengths. There may be amplification agents, however, that initiate synthesis at the 5'-end and proceed in the other direction, using the same process as described above. In any event, the process of the invention is not to be limited to the embodiments of amplification described herein.

One process of in vitro amplification, which is used according to this invention, is the polymerase chain reaction (PCR) described in U.S. Pat. Nos. 4,683,202 and 4,683,195.

The term "polymerase chain reaction" refers to a process for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. Many polymerase chain processes are known to those of skill in the art and may be used in the process of the invention. For example, DNA is subjected to 30 to 35 cycles of amplification in a thermocycler as follows: 95° C. for 30 sec, 52 to 60° C. for 1 min, and 72° C. for 1 min, with a final extension step of 72° C. for 5 min. For another example, DNA is subjected to 35 polymerase chain reaction cycles in a thermocycler at a denaturing temperature of 95° C. for 30 sec, followed by varying annealing temperatures ranging from 54 to 58° C. for 1 min, an extension step at 70° C. for 1 min, with a final extension step at 70° C. for 5 min.

The primers for use in amplifying the mRNA or genomic RNA of HRV may be prepared using any suitable process, such as conventional phosphotriester and phosphodiester processes or automated embodiments thereof so long as the primers are capable of hybridizing to the nucleic acid sequences of interest. One process for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the process of the invention are complementary to each strand of nucleotide sequence to be amplified. The term "complementary" means that the primers must hybridize with their respective strands under conditions, which allow the agent for polymerization to function. In other words, the primers that are complementary to the flanking sequences hybridize with the flanking sequences and permit amplification of the nucleotide sequence. Preferably, the 3' terminus of the primer that is extended is perfectly base paired with the complementary flanking strand. Preferably, probes possess nucleotide sequences complementary to one or more strands of the 5'-NCR of HRV. More preferably, the primers are complementary to HRV genetic sequences encompassing positions 300-600. Most preferably, primers contain the nucleotide sequences of SEQ ID NOS: 1 and 2. It is appreciated that the complement of SEQ ID NOS: 1 and 2 are similarly suitable for use in the instant invention. It is further appreciated that oligonucleotide sequences that hybridize with SEQ ID NO: 1 or 2 are also similarly suitable. Finally, multiple positions are available for hybridization on the HRV genome and will be also suitable hybridization with a probe when used with the proper forward and reverse primers.

Those of ordinary skill in the art will know of various amplification processes that can also be utilized to increase the copy number of target HRV nucleic acid sequence. The nucleic acid sequences detected in the process of the invention are optionally further evaluated, detected, cloned, sequenced, and the like, either in solution or after binding to a solid support, by any process usually applied to the detection of a specific nucleic acid sequence such as another polymerase chain reaction, oligomer restriction (Saiki et al., *BioTechnology* 3:1008 1012 (1985)), allele-specific oligonucleotide (ASO) probe analysis (Conner et al., *PNAS* 80: 278 (1983)), oligonucleotide ligation assays (OLAs) (Landegren et al., *Science* 241:1077 (1988)), RNase Protection Assay and the like. Molecular techniques for DNA analysis have been reviewed (Landegren et al., *Science* 242:229 237 (1988)). Following DNA amplification, the reaction product may be detected by Southern blot analysis, without using radioactive probes. In such a process, for example, a small sample of DNA containing the nucleic acid sequence obtained from the tissue or subject is amplified, and analyzed via a Southern blotting technique. The use of non-radioactive probes or labels is facilitated by the high level of the amplified signal. In one embodiment of the invention, one nucleoside triphosphate is radioactively labeled, thereby allowing direct visualization of the amplification product by autoradiography. In another embodiment, amplification primers are fluorescently labeled and run through an electrophoresis system. Visualization of amplified products is by laser detection followed by computer assisted graphic display, without a radioactive signal.

Other methods of detection amplified oligonucleotide illustratively include gel electrophoresis, mass spectrometry, liquid chromatography, fluorescence, luminescence, gel mobility shift assay, fluorescence resonance energy transfer, nucleotide sequencing, enzyme-linked immunoadsorbent assay, affinity chromatography, chromatography, immunoenzymatic methods (Ortiz, A and Ritter, E, *Nucleic Acids Res.*, 1996; 24:3280-3281), streptavidin-conjugated enzymes, DNA branch migration (Lishanski, A, et al., *Nucleic Acids Res.*, 2000; 28(9):e42), enzyme digestion (U.S. Pat. No. 5,580,730), colorimetric methods (Lee, K., *Biotechnology Letters*, 2003; 25:1739-1742), or combinations thereof.

The term "labeled" with regard to the probe is intended to encompass direct labeling of the probe by coupling (i.e., physically linking) a detectable substance to the probe, as well as indirect labeling of the probe by reactivity with another reagent that is directly labeled. Examples of indirect labeling include detection of a probe using a fluorescently labeled antibody and end-labeling or centrally labeling of a DNA probe with biotin such that it can be detected with fluorescently labeled streptavidin. The detection method of the invention can be used to detect RNA (particularly mRNA) or genomic nucleic acid in a sample in vitro as well as in vivo. For example, in vitro techniques for detection of nucleic acid include northern hybridizations, in situ hybridizations, RT-PCR, real-time RT-PCR, and DNase protection. In vitro techniques for detection of genomic nucleic acid include northern hybridizations, RT-PCR, real-time RT-PCR, and DNase protection. Furthermore, in vivo techniques for detection of HRV include introducing into a subject organism a labeled antibody directed against a capsid or polypeptide component or directed against a particular nucleic acid sequence of HRV. For example, the antibody can be labeled with a radioactive marker whose presence and location in the subject organism can be detected by standard imaging techniques, including autoradiography.

The size of the primers used to amplify a portion of the nucleic acid sequence of HRV is at least 5, and often 10, 15, 20, 25, or 30 nucleotides in length. Preferably, the GC ratio should be above 30%, 35%, 40%, 45%, 50%, 55%, or 60% so as to prevent hair-pin structure on the primer. Furthermore, the amplicon should be sufficiently long enough to be detected by standard molecular biology methodologies. The forward primer is preferably shorter than the reverse primer. Techniques for modifying the $T_m$ of either primer are operable herein. An illustrative forward primer contains LNAdA and LNA-dT (Glen Research Corporation) so as to match $T_m$ with a corresponding alternate primer.

An inventive process uses a polymerization reaction which employs a nucleic acid polymerizing enzyme, illustratively a DNA polymerase, RNA polymerase, reverse transcriptase, or mixtures thereof It is further appreciated that accessory proteins or molecules are present to form the replication machinery. In a preferred embodiment the polymerizing enzyme is a thermostable polymerase or thermodegradable polymerase. Use of thermostable polymerases is well known in the art such as Taq polymerase available from Invitrogen Corporation. Thermostable polymerases allow a polymerization reaction to be initiated or shut down by changing the temperature other condition in the reaction mixture without destroying activity of the polymerase.

Accuracy of the base pairing in the preferred embodiment of DNA sequencing is provided by the specificity of the enzyme. Error rates for Taq polymerase tend to be false base incorporation of $10^{-5}$ or less. (Johnson, *Annual Reviews of Biochemistry*, 1993: 62:685-713; Kunkel, *Journal of Biological Chemistry*, 1992; 267:18251-18254). Specific examples of thermostable polymerases illustratively include those isolated from *Thermus aquaticus, Thermus thermophilus, Pyrococcus woesei, Pyrococcus furiosus, Thermococcus litoralis* and *Thermotoga maritima*. Thermodegradable polymerases illustratively include *E. coli* DNA polymerase, the Klenow fragment of *E. coli* DNA polymerase, T4 DNA polymerase, T7 DNA polymerase and other examples known in the art. It is recognized in the art that other polymerizing enzymes are similarly suitable illustratively including *E. coli*, T7, T3, SP6 RNA polymerases and AMV, M-MLV, and HIV reverse transcriptases.

The polymerases are optionally bound to the primer. When the HRV is a single-stranded DNA molecule due to heat denaturing the polymerase is bound at the primed end of the single-stranded nucleic acid at an origin of replication. A binding site for a suitable polymerase is optionally created by an accessory protein or by any primed single-stranded nucleic acid.

In a further embodiment detection of PCR products is achieved by mass spectrometry. Mass spectrometry has several advantages over RT-PCR or real-time RT=PCR systems in that it can be used to simultaneously detect the presence of HRV and decipher mutations in target nucleic acid sequences allowing identification and monitoring of emerging strains. Further, mass spectrometers are prevalent in the clinical laboratory. Similar to fluorescence based detection systems mass spectrometry is capable of simultaneously detecting multiple amplification products for a multiplexed and controlled approach to accurately quantifying components of biological or environmental samples.

Multiple mass spectrometry platforms are suitable for use in the instant invention illustratively including matrix assisted laser desorption ionization time of flight mass spectrometry (MALDI), electrospray mass spectrometry, electrospray ionization-Fourier transform ion cyclotron resonance mass spectrometry (ESI-FTICR), multi-stage mass spectrometry fragmentation analysis (MS/MS), mass spectrometry coupled with liquid chromatography such as high performance liquid chromatography mass spectrometry (HPLC) and ultra performance liquid chromatography isotope dilution tandem mass spectrometry (UPLC-ID/MS/MS), and variations thereof.

It is appreciated that numerous other detection processes are similarly suitable for measuring an amplification product by detecting a detection signal. Illustrative examples include, but are not limited to, liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, real-time PCR (RT-PCR), gel electrophoresis, or combinations thereof.

Preferably, PCR amplification products are generated using complementary forward and reverse oligonucleotide primers. In a non-limiting example, HRV genetic sequences or fragments thereof are amplified by the primer pair SEQ ID NOS: 1 and 2 that amplify a conserved sequence in the HRV 5'-NCR encompassing nucleotides 356-563. The resulting amplification product is processed and prepared for detection by processes known in the art. It is appreciated that the complements of SEQ ID NOS: 1 and 2 are similarly suitable for use in the instant invention. It is further appreciated that oligonucleotide sequences that hybridize with SEQ ID NO: 1 or 2 are also similarly suitable. Finally, multiple positions are available for hybridization on the HRV genome and will be also suitable hybridization with forward and reverse primers that may or may not be used with a probe for real-time RT-PCR.

Optionally, multiple amplification products are simultaneously produced in a PCR reaction that is then available for simultaneous detection and quantification. Thus, multiple detection signals are inherently produced or emitted that are separately and uniquely detected in one or more detection systems. It is appreciated that multiple detection signals are optionally produced in parallel. Preferably, a single biological sample is subjected to analysis for the simultaneous or sequential detection of HRV genetic sequences. It is appreciated that three or more independent or overlapping sequences are simultaneously or sequentially measured in the instant inventive process. Oligonucleotide matched primers (illustratively SEQ ID NOS: 1 and 2) are simultaneously or sequentially added and the biological sample is subjected to proper thermocycling reaction parameters. For detection by mass spectrometry a single sample of the amplification products from each gene are simultaneously analyzed allowing for rapid and accurate determination of the presence of HRV. Optionally, analysis by real-time RT-PCR is employed capitalizing on multiple probes with unique fluorescent signatures. Thus, each gene is detected without interference by other amplification products. This, multi-target approach increases confidence in quantification and provides for additional internal control.

In a specific embodiment, the processes further involve obtaining a control sample from a control subject, contacting the control sample with a compound or agent capable of detecting the presence of HRV nucleic acid in the sample, and comparing the presence of mRNA or genomic RNA in the control sample with the presence of mRNA or genomic DNA in the test sample.

The invention also encompasses kits for detecting the presence of HRV viral nucleic acids in a test sample. The kit, for example, includes a labeled compound or agent capable of detecting a nucleic acid molecule in a test sample and, in certain embodiments, for determining the titer in the sample.

For oligonucleotide-based kits, the kit includes for example: (1) an oligonucleotide, e.g., a detectably labeled oligonucleotide, which hybridizes to a nucleic acid sequence of the HRV virus and/or (2) a pair of primers (one forward and one reverse) useful for amplifying a nucleic acid molecule containing the HRV viral sequence. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which is assayed and compared to the test sample contained. Each component of the kit is usually enclosed within an individual container and all of the various containers are usually enclosed within a single package along with instructions for use.

The instant inventive processes are amenable to use for diagnosis of HRV infection in a subject, insects, and any inclusive other organism capable of infection or transfection by or with HRV.

To increase confidence and to serve as an internal or external control, a purified and titered HRV solution is used as a biological sample. By amplification of a single sample with known quantities of HRV or of a set of samples representing a titration of HRV, the level of HRV in the unknown biological sample is determined. Preferably, the purified and titered HRV solution is analyzed in parallel with the unknown biological sample to reduce inter assay error or to serve as a standard curve for quantitation of unknown HRV in the biological sample. Using purified and titered HRV solution provides for a similar complete genetic base DNA strand for amplification.

In another embodiment, a subgenomic fragment is cloned into a plasmid for amplification, purification, and use as a quantitative comparator or nucleic acid calibrator. In a non-limiting example, a DNA subgenomic fragment of HRV is optionally amplified from a positive nasal swab using primers bracketing the RT-PCR target regions in the 5'-NCR of HRV. It is appreciated that other sequences are similarly suitable for use as a quantitative control. The known concentration of the subgenomic fragment is used to create a standard curve for quantitative determinations and to access amplification efficiency.

Also provided is a kit for detecting HRV infection that contains reagents for the amplification, or direct detection of HRV or portions thereof. An exemplary kit illustratively includes a forward and reverse primer pair, a non-degenerate probe. In a preferred embodiment, the forward and reverse primers have the oligonucleotide sequence SEQ ID NOS: 1 and 2 and a nondegenerate probe of the sequence SEQ ID NO: 3. It is appreciated that a diagnostic kit may optionally contain primers and probes that are the complements of SEQ ID NOS: 1-3 or that hybridize with oligonucleotides SEQ ID NOS: 1-3. It is further appreciated that a diagnostic kit optionally includes ancillary reagents such as buffers, solvents, thermostable polymerases, nucleotides, and other reagents necessary and recognized in the art for amplification and detection of HRV in a biological sample.

The invention provides a host cell containing a nucleic acid sequences according to the invention as an alternative to synthetic primer sequence generation. Plasmids containing the polymerase components of the HRV virus are generated in prokaryotic cells for the expression of the components in relevant cell types (bacteria, insect cells, eukaryotic cells). Preferably, the cell line is a primate cell line. These cell lines may be cultured and maintained using known cell culture techniques such as described in Celis, Julio, ed., 1994, Cell Biology Laboratory Handbook, Academic Press, NY. Various culturing conditions for these cells, including media formulations with regard to specific nutrients, oxygen, tension, carbon dioxide and reduced serum levels, can be selected and optimized by one of skill in the art.

The preferred cell line of the present invention is a eukaryotic cell line, preferably an insect cell line, such as SD per, transiently or stably expressing one or more full-length or partial HRV proteins. Such cells can be made by transfection (proteins or nucleic acid vectors), infection (viral vectors) or transduction (viral vectors). The cell lines for use in the present invention are cloned using known cell culture techniques familiar to one skilled in the art. The cells are cultured and expanded from a single cell using commercially available culture media under known conditions suitable for propagating cells.

A host cell is a cell derived from a mammal, insect, yeast, bacteria, or any other single or multicellular organism recognized in the art. Host cells are optionally primary cells or immortalized derivative cells. Immortalized cells are those which can be maintained in-vitro for several replication passages.

In a most preferred embodiment, an HRV antigen such as an amino acid sequence representative of a capsid protein is used as a control for a PCR based assay for the detection and measurement of the presence of HRV in a biological sample. The process of detecting HRV antibodies in a biological sample is optionally performed in parallel with the same or control biological samples that are used to detect HRV genetic sequences.

A kit for detection of HRV infection in a patient optionally contains reagents for PCR based detection of HRV genetic sequences, either structural or non-structural, and optionally for detection of antibodies directed to structural HRV proteins. The components of the kits are any of the reagents described above or other necessary and non-necessary reagents known in the art for solubilization, detection, washing, storage, or other need for in a diagnostic assay kit.

The present invention is further illustrated with respect to the following non-limiting examples. The following examples are for illustrative purposes only and are not a limitation on the practice or scope of the invention.

EXAMPLE 1

Figure 1:
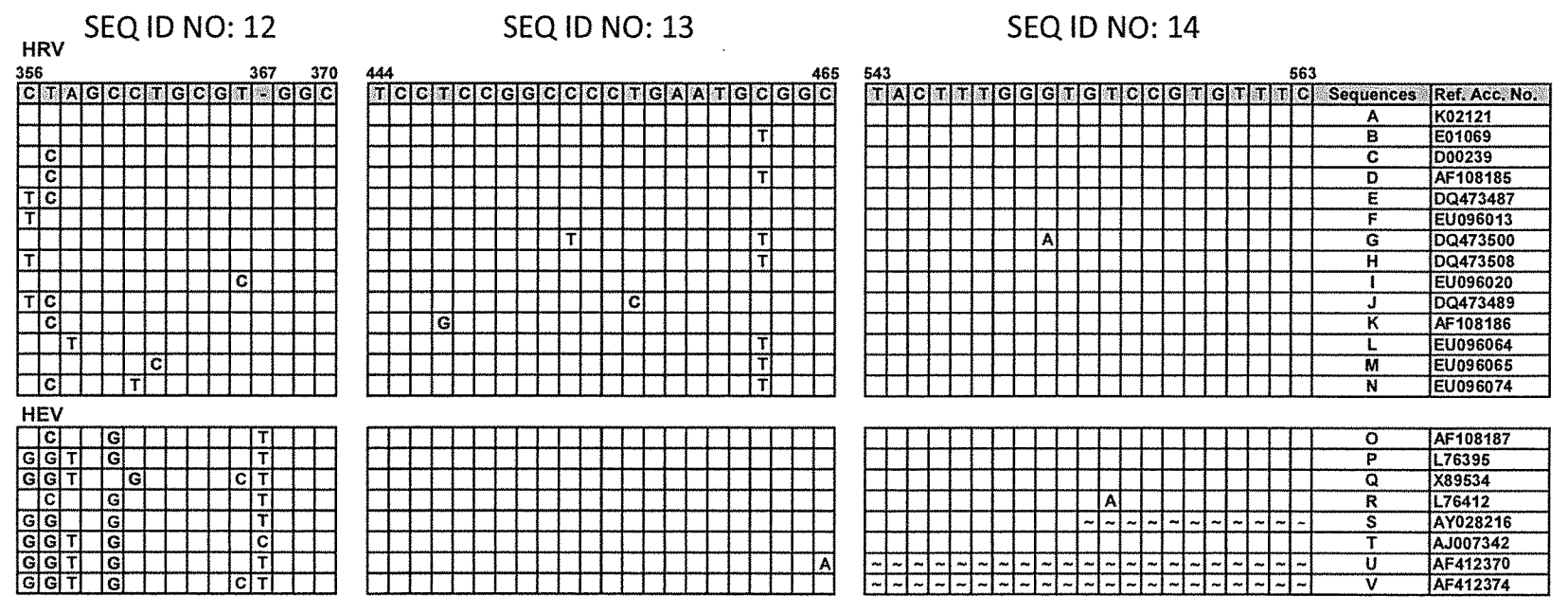

Obtaining viral strains and clinical specimens. One hundred HRV prototype strains (strains identification 1A, 1B, 2-86, 88-100) (numbering refers to strain assignment number as illustrated in FIG. 1 and the description thereof) are kindly obtainable from ViroPharma Inc. (Ledford, R. M., *J. Viral.*, 2004; 78:3661-3674) and 85 HRV field isolates obtained from several sources between 1999 and 2007 were available for study. HRV isolates are either sequenced directly or subjected to a single passage in HeLa Ohio cells.

For cell culture, infected cells are incubated at 35° C. in 5% $CO_2$ with gentle rocking until reaching full cytopathic effect. Isolates are freeze-thawed twice, clarified by low speed centrifugation and supernatants collected and stored at −70° C. In one study 48 HEV laboratory strains were grown in primary monkey kidney or human RD cells and prepared as above. The studied strains included echoviruses 1-6, 8, 9, 11-25, 29-31; coxsackievirus types A2, A4-6, A8-10, A16, A21, A24, B1-6; enterovirus types 68, 70, 71; and poliovirus types 1, 2 and 3. Other respiratory viruses are subjected to testing for specificity including respiratory syncytial virus, human metapneumovirus, human parainfluenza viruses 1-4, adenovirus, coronaviruses 229E and OC43, influenza viruses A and B, and human bocavirus (Lu, X., *J. Clin. Microbiol.*, 2006; 44:3231-3235). Coded respiratory specimens that were culture positive for HRV or HEV were provided by California Department of Health Services, University of Washington, Vanderbilt Medical Center, and University of Rochester Medical Center for clinical validation studies. Nasal and throat swab specimens are self-obtained by symptomatic volunteers or obtained clinically. These specimens are expressed in 2 ml of chilled viral transport media (Hank's buffered salt solution with 0.5% gelatin) and frozen at −70° C. prior to testing.

EXAMPLE 2

Preparation of nucleic acid and sequencing of viral strains. To identify conserved regions of the sample viral strains all HRV and HEV viral strains obtained as in Example 1 are subjected to nucleotide sequencing.

Total nucleic acid extracts from all samples collected or obtained as in Example 1 are prepared from 100 μl of infected cell culture lysate or 200 μl of clinical specimen using the NucliSens® easyMAG™ extraction system following manufacturer's instructions (bioMérieux, Durham, N.C.).

The 5'NCR of viral strains was sequenced to identify conserved regions. Extracted viral RNA is reverse transcribed using random hexamer primers (Promega, Madison, Wis.) at 52° C. for 60 min with Superscript™ III Reverse Transcriptase (Invitrogen, Carlsbad, Calif.) following manufacturer's instructions. Five μl of the obtained cDNA is amplified in two separate PCR reactions using HRV species A (SEQ ID NOS: 4 and 5) and B specific amplification primer sets (SEQ ID NOS: 6 and 7) (Table 1) with the HotStarTaq Master Mix Kit (Qiagen, Chatsworth, Calif.). PCR cycling conditions are as follows: initial activation step at 95° C. for 15 min followed by 35 cycles of 95° C. for 1 min, 55° C. for 1 min and 72° C. for 1 min, with a final extension of 72° C. for 5 min on a GeneAmp® PCR System 9700 (Applied Biosystems). Amplified products are subjected to purification with the QIAquick® PCR Purification Kit (Qiagen). Sequencing is performed in both directions using the amplification primers and the ABI Prism® Bigdye™ Terminator Cycle Sequencing Ready Reaction Kit ver. 3.1 on an ABI 3100 DNA Sequencer (Applied Biosystems). Sequence assembly and editing is accomplished using Sequencher™ ver. 3.1.1 software (Gene Codes, Ann Arbor, Mich.).

All obtained sequences are aligned along with previously identified sequences of representative HRV/HEV strains available from GenBank (NIH). As demonstrated in FIG. 1, the alignment identified a conserved region within the 5'NCR between nucleotide positions 356 and 563 (numbering relative to HRV1B accession no. D00239). Subregions were identified to design real-time RT-PCR primer pairs for subsequent evaluation. The most preferred primer pair are represented by SEQ ID NOS: 1 and 2. The forward primer (SEQ ID NO: 1) is located in a variable region that contains a signature "T" indel at nt position 367. This indel distinguishes all HRVs from HEVs and is exploited for differential amplification and identification. The forward primer is necessarily shorter in length due to the lower conservation of this region of the 5'NCR. To compensate LNA-dA and LNA-dT is introduced into the primer at positions 3 and 7 respectively to achieve a balanced $T_m$ with the reverse primer. It is appreciated that other modifications including sequence length, chemical and other modifications are similarly operable. Real-time RT-PCR is optimally achieved using the iScript™ One-step RT-PCR Kit for Probes (Bio-Rad). Other commercial real-time RT-PCR reagent kits performed equally or less optimally. The QuantiTect Probe PCR Kit (Qiagen) and Ag-Path-ID™ One-Step RT-PCR Kit (Applied Biosystems) performs comparably, whereas amplification is less efficient with the TaqMan® One-Step RT-PCR Master Mix (Applied Biosystems). Real-time RT-PCR is unsuccessful using SuperScript™ III Platinum One-Step qRT-PCR Kit (Invitrogen).

EXAMPLE 3

Real-time RT-PCR to identify HRV and distinguish HEV. The real-time RT-PCR assay is optimally performed using iScript™ One-Step RT-PCR Kit for Probes (Bio-Rad, Hercules, Calif.). The reaction is performed in 25 μl final volume containing 1 μM forward and reverse primers, 0.1

TABLE 1

HRV/HEV primers and probes.

| Primer/Probe[a] | Sequence (5'-3')[b] | Position |
|---|---|---|
| Real time RT-PCR | | |
| Primer, fwd | CPXGCCZGCGTGGY (SEQ ID NO: 1) where Y is C | 356-369[c] |
| Primer, rev | GAAACACGGACACCCAAAGTA (SEQ ID NO: 2) | 563-543[c] |
| Probe | TCCTCCGGCCCCTGAATGYGGC (SEQ ID NO: 3) | 444-465[c] |
| HRVA 5'NCR sequencing | | |
| Primer, fwd | GTACTCTGTTATTCCGGTAACTTTGYAYGCCA (SEQ ID NO: 4) | 49-80[c] |
| Primer, rev | CCAACATTCTGTCTAGATACYTGDGCVCCCAT (SEQ ID NO: 5) | 655-623[c] |
| HRVB 5'NCR sequencing | | |
| Primer, fwd | ACTCTGGTACTATGTACCTTTGTACGCCTGTT (SEQ ID NO: 6) | 48-80[d] |
| Primer, rev | CCACTCTTCTGTGTAGACACYTGDGCDCCCAT (SEQ ID NO: 7) | 661-629[d] |
| HRV14 RNA transcript | | |
| Primer, fwd-T7 | <u>TAATACGACTCACTATAGGG</u>CAAGCACTTCTGTTT (SEQ ID NO: 8) | 179-193[d] |
| Primer, rev-SP6 | <u>ATTTAGGTGACACTATAGAA</u>GCATCTGGTAATTCC (SEQ ID NO: 9) | 1089-1074[d] |
| HEV68 RNA transcript | | |
| Primer, fwd-T7 | <u>TAATACGACTCACTATAGGG</u>TCTTATGAGCAAGCACT (SEQ ID NO: 10) | 52-68[e] |
| Primer, rev-SP6 | <u>ATTTAGGTGACACTATAGAA</u>ATTACTTCAAAATAACTCAG (SEQ ID NO: 11) | 573-554[e] |

[a]Probes 5'-end-labeled with 6-carboxyfluorescein (FAM) and 3'-end-labeled with Black Hole Quencher™
[b]Y = dC or dT, D = dA, dT or dG, V = dA, dC or dG, P = pyrimidine derivative, a degenerate base mimicking a C/T mix (Glen Research Corporation, Archive Report 8.1), X = LNA-dA, Z = LNA-dT (Glen Research Corporation, Archive Report 20.1); underlined sequences are T7 and SP6 promoter sites
[c]Nucleotide numbering based on HRV1B (accession no. D00239)
[d]Nucleotide numbering based on HRV14 (accession no. K02121)
[e]Nucleotide numbering based on HEV68 (formally HRV87) (accession no. AY062273)

μM probe, and 5 μl of nucleic acid extract with the remaining volume made of buffer. Amplification is performed on an iCycler iQ Real-Time Detection System (Bio-Rad) using the following thermocycling conditions: 10 min at 48° C. for reverse transcription; 3 min at 95° C. for polymerase activation; and 45 cycles of 15 s at 95° C.; and 1 min at 60° C.

Undiluted RNA extracts of all HRV prototype strains and field isolates produce strongly positive reactions [median cycle threshold (Ct) value 13.7, range 9.3-25.3]. The assay is specific and robust for HRV in that 34 HEVs are nonreactive and 14 (Echo1, 3, 5, 6, 13, 21; Polio1, 2; EV68, 71; CoxA4, 6, 24; CoxB1) produce only weakly positive reactions (median Ct value 34, range 33-34.8); and may be related to virus titer.

Assay sensitivity is determined by comparison of serial dilutions of representative HRV strains and other viral strains. Serial ten-fold dilutions of HRV14 RNA transcripts that show 100% sequence identity to the real-time RT-PCR primers and probe set (SEQ ID NOS: 1-3) are compared to HEV and other representative viruses. With HRV14 linear amplification is achieved over a 7-log dynamic range from $5 \times 10^1$ to $5 \times 10^7$ copies per reaction. The assay's detection limit with 24 replicates of is 100% positive at 50 copies; at 5 copies, 37.5% positive at 9 copies; and at 1 copy, 2 (8.3%) were positive. In contrast, the HEV68 transcript is undetectable below approximately $5 \times 10^5$ copies per reaction. Nucleic acid extracts of other respiratory viruses, including human respiratory syncytial virus, human metapneumovirus, parainfluenza viruses 1-4, adenovirus, coronaviruses 229E and OC43, influenza A and B, and human bocavirus are negative by the inventive real-time RT-PCR assay.

Over the linear range of the assay, the coefficient of variation of the mean Ct values ranged from 0.24% to 0.94% within runs, and from 0.91% to 2.68% between runs demonstrating robust reproducibility. (FIG. 2.)

EXAMPLE 4

Use of the real-time RT-PCR assay for identification of HRV in clinical samples. Extracts of 111 coded respiratory specimens previously determined to be culture positive for HRV or HEV are prepared and tested simultaneously by the inventive HRV real-time RT-PCR assay and compared to results obtained from two independent laboratories using different in-house HRV/HEV RT-PCR assays. Of 87 HRV culture-positive specimens tested, all are identified as HRV by the inventive real-time RT-PCR assay (median Ct value 26.3; range 14.9-38.5); HRV is also identified in all 87 specimens by one or both of the reference in-house RT-PCR assays. Of 24 HEV culture-positive specimens, 4 are positive for HRV by the real-time RT-PCR assay (median Ct value 28.8; range 26.2-32.1); 1 of these 4 was also identified as HRV by laboratory B. HEV isolates available from 3 of the 4 HRV positive specimens were not amplified by the inventive real-time RT-PCR assay, whereas amplicon sequences obtained from all 4 clinical specimens were HRV positive suggesting that both HRV and HEV were present in these specimens.

Figure 3:
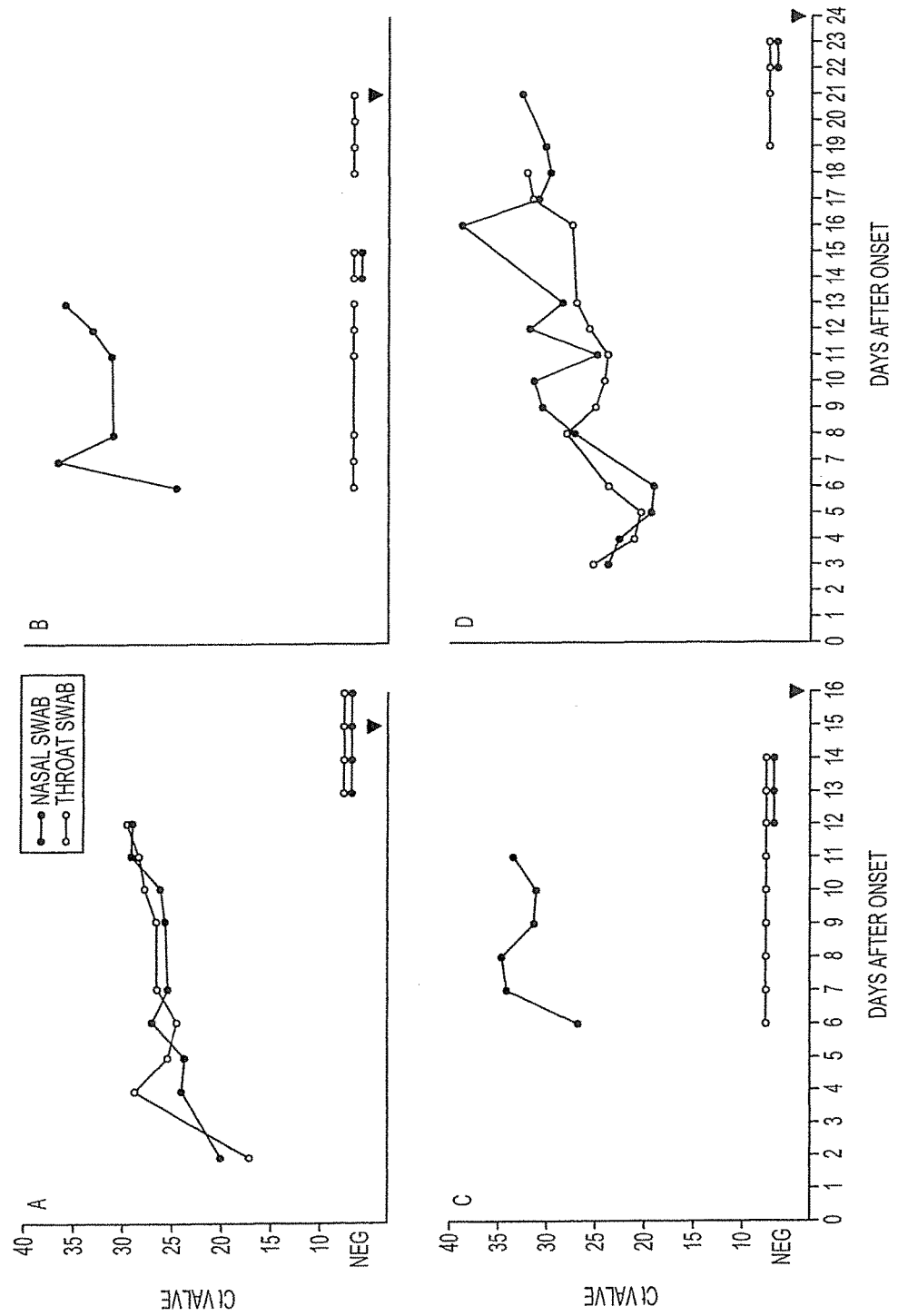
FIG. 3 represents HRV detected by the inventive real-time RT-PCR assay in serial nasal and throat swab specimens from 4 HRV positive donors (A, B, C and D) with acute respiratory illness.

To access the inventive real-time RT-PCR assay in clinical specimens of nasal or throat swabs, volunteers who developed respiratory illnesses characterized by one or more of the following symptoms: cough, congestion, myalgia, chills or fever, donated self-collected samples. The inventive real-time RT-PCR identified 5 cases with HRV infection. Collection began 2 and 6 days after onset of symptoms and continued until at least 2 consecutive specimens tested negative (FIG. 3). The duration of detectable HRV ranged from 11 to 21 days (median 12.5 days). With the exception of case A, where HRV was detected at comparable levels from both throat and nasal swabs, throat swabs were either consistently negative for HRV (cases B and C) or became negative earlier than from nasal swabs (case D). The duration of symptoms for five HRV positive cases ranged from 12 to 24 days (median 16 days); one case (D) had a prolonged paroxysmal cough that persisted for 24 days. The duration of reported symptoms exceeded the duration of detectable HRV by the inventive real-time RT-PCR assay for all cases. Sequencing of a partial region of the HRV VP1 gene from the specimens obtained from the 5 cases identified two genetically distinct HRV strains that showed the closest sequence identities to HRV86 (amino acid identity score 83.5%) and HRV69 (amino acid identity score 84.6%), respectively.

EXAMPLE 5

Detection of HRV amplicons via mass spectroscopy. Detection of amplification products obtained as in Example 3 was performed essentially as described by Blyn, L, et al. *J. Clin. Microbial.* 2008; 46(2):644-651. Following amplification each PCR mixture is desalted and purified using a weak anion-exchange protocol based on the method of Jiang and Hofstadler (Jiang, Y., and S. A. Hofstadler. *Anal. Biochem.* 2003; 316:50-57). ESI-TOF is used to obtain accurate-mass (±1 ppm), high-resolution (M/ΔM, >10,000 full width half maximum) mass spectra. For each sample, approximately 1.5 μl of analyte solution is consumed during the spectral acquisition. Raw mass spectra are postcalibrated with an internal mass standard and deconvolved to average molecular masses. Quantitative results are obtained by comparing the peak heights with an internal PCR calibration standard present in every PCR well at 300 molecules unless otherwise indicated.

Patent applications and publications mentioned in the specification are indicative of the levels of those skilled in the art to which the invention pertains. The foregoing description is illustrative of particular embodiments of the invention, but is not meant to be a limitation upon the practice thereof The following claims, including all equivalents thereof, are intended to define the scope of the invention.

The invention is hereby described with relation to the following references and those otherwise identified in the instant specification. Each reference is incorporated herein by reference as if each were laid out explicitly in its entirety in the instant specification including both text and figures. Each reference is incorporated for the individual point referred to in the specification as well as for all information contained therein and not explicitly identified in the specification. All references are representative of the knowledge of a person of skill in the art and illustrate other aspects of the present invention as envisioned by the inventors.

REFERENCE LIST

1. Andeweg, A. C., T. M. Bestebroer, M. Huybreghs, T. G. Kimman, and J. C. de Jong. 1999. Improved detection of rhinoviruses in clinical samples by using a newly developed nested reverse transcription-PCR assay. *J. Clin. Microbiol.* 37:524-530
2. Andries, K., B. Dewindt, J. Snoeks, L. Wouters, H. Moereels, P. J. Lewi, and P. A. Janssen. 1990. Two groups of rhinoviruses revealed by a panel of antiviral compounds present sequence divergence and differential pathogenicity. *J. Virol.* 64:1117-1123.
3. Atmar, R. L., and P. R. Georghiou. 1993. Classification of respiratory tract picornavirus isolates as enteroviruses or rhinoviruses by using reverse transcription-polymerase chain reaction. *J. Clin. Microbial.* 31:2544-2546.
4. Billaud, G., S. Peny, V. Legay, B. Lina, and M. Valette. 2003. Detection of rhinovirus and enterovirus in upper respiratory tract samples using a multiplex nested PCR. *J. Virol. Methods* 108:223-228.
5. Blomqvist, S., A. Skytta, M. Roivainen, and T. Hovi. 1999. Rapid detection of human rhinoviruses in nasopharyngeal aspirates by a microwell reverse transcription-PCR-hybridization assay. *J. Clin. Microbiol.* 37:2813-2816.
6. Blomqvist, S., C. Savolainen, L. Raman, M. Roivainen, and T. Hovi. 2002. Human rhinovirus 87 and enterovirus 68 represent a unique serotype with rhinovirus and enterovirus features. *J. Clin. Microbiol.* 40:4218-4223.
7. Corless, C. E., M. Guiver, R. Borrow, V. Edwards-Jones, A. J. Fox, E. B. Kaczmarski, and K. J. Mutton. 2002. Development and evaluation of a 'real-time' RT-PCR for the detection of enterovirus and parechovirus RNA in CSF and throat swab samples. *J. Med. Virol.* 67:555-562.
8. Dagher, H., H. Donninger, P. Hutchinson, R. Ghildyal, and P. Bardin. 2004. Rhinovirus detection: comparison of real-time and conventional PCR. *J. Viral. Methods.* 117:113-121.
9. Deffernez, C., W. Wunderli, Y. Thomas, S. Yerly, L. Perrin, and L. Kaiser. 2004. Amplicon sequencing and improved detection of human rhinovirus in respiratory samples. *J. Clin. Microbiol.* 42:3212-3218.
10. Emery, S. L., D. D. Erdman, M. D. Bowen, B. R. Newton, J. M. Winchell, R. F. Meyer, S. Tong, B. T. Cook, B. P. Holloway, K. A. McCaustland, P. A. Rota, B. Bankamp, L. E. Lowe, T. G. Ksiazek, W. J. Bellini, and L. J. Anderson. 2004. Real-time reverse transcription-polymerase chain reaction assay for SARS-associated coronavirus. *Emerg. Infect. Dis.* 10:311-316.
11. Fox, J. P., M. K. Cooney, C. E. Hall, and H. M. Foy. 1985. Rhinoviruses in Seattle families, 1975-1979. *Am. J. Epidemiol.* 122:830-846.
12. Friedlander, S. L., and W. W. Busse. 2005. The role of rhinovirus in asthma exacerbations. *J. Allergy. Clin. Immunol.* 116:267-273.
13. Ghosh, S., R. Champlin, R. Couch, J. England, I. Raad, S. Malik, M. Luna, and E. Whimbey. 1999. Rhinovirus infections in myelosuppressed adult blood and marrow transplant recipients. *Clin. Infect. Dis.* 29:528-532.
14. Halonen, P., E. Rocha, J. Hierholzer, B. Holloway, T. Hyypia, P. Hurskainen, and M. Pallansch. 1995. Detection of enteroviruses and rhinoviruses in clinical specimens by PCR and liquid-phase hybridization. *J. Clin. Microbiol.* 33:648-653.
15. Hendley, J. O., and J. M. Gwaltney 1988. Mechanisms of transmission of rhinovirus infections. *Epidemiol. Rev.* 10:243-258.
16. Hicks, L. A., C O W. Sheppard, P. H. Britz, D. D. Erdman, M. Fischer, B. L. Flannery, A. J. Peck, X. Lu, W. L. Thacker, R. F. Benson, M. L. Tondella, M. E. Moll, C. G. Whitney, L. J. Anderson, and D. R. Feikin. 2006. Two outbreaks of severe respiratory disease in nursing homes associated with rhinovirus. *J. Am. Geriatr. Soc.* 54:284-289.
17. Hyypia, T., T. Puhakka, O. Ruuskanen, M. Makela, A. Arola, and P. Arstila. 1998. Molecular diagnosis of human rhinovirus infections: comparison with virus isolation. *J. Clin. Microbiol.* 36:2081-2083.
18. Ireland, D. C., J. Kent, and K. G. Nicholson. 1993. Improved detection of rhinoviruses in nasal and throat swabs by seminested RT-PCR. *J. Med. Virol.* 40:96-101.
19. Ison, M. G., F. G. Hayden, L. Kaiser, L. Corey, and M. Boeckh. 2003. Rhinovirus infections in hematopoietic stem cell transplant recipients with pneumonia. *Clin. Infect. Dis.* 36:1139-1143.
20. Jartti, T., P. Lehtinen, T. Vuorinen, M. Koskenvuo, and O. Ruuskanen. 2004. Persistence of rhinovirus and enterovirus RNA after acute respiratory illness in children. *J. Med. Virol.* 72:695-699.
21. Johnston, S. L., and D. A. J. Tyrreil. 1995. Rhinoviruses, p. 553-563. In E. H. Lennette, D. A. Lennette, and E. T. Lennette (ed.), Diagnostic Procedures for Viral, Rickettsial, and Chlamydial Infections, 7th ed. American Public Health Association, Washington, D.C.
22. Joki-Korpela, P., and T. Hyypia. 2001. Parechoviruses, a novel group of human picomaviruses. *Ann. Med.* 33:466-471.
23. Kaiser, L., J. D. Aubert, J. C. Pache, C. Deffernez, T. Rochat, J. Garbino, W. Wunderli, P. Meylan, S. Yerly, L. Perrin, I. Letovanec, L. Nicod, C. Tapparel, and P. M. Soccal. 2006. Chronic rhinoviral infection in lung transplant recipients. *Am. J Respir. Crit. Care. Med.* 174:1392-1399.
24. Kammerer, U., B. Kunkel, and K. Korn. 1994. Nested PCR for specific detection and rapid identification of human picornaviruses. *J. Clin. Microbial.* 32:285-291.
25. Kares, S., M. Lonnrot, P. Vuorinen, S. Oikarinen, S. Taurianen, and H. Hyoty. 2004. Real-time PCR for rapid diagnosis of entero- and rhinovirus infections using LightCycler. *J. Clin. Virol.* 29:99-104.
26. Khetsuriani, N., N. N. Kazerouni, D. D. Erdman, X. Lu, S. C. Redd, L. J. Anderson, and W. G. Teague. 2007. Prevalence of viral respiratory tract infections in children with asthma. *J. Allergy. Clin. Immunol.* 119:314-321.
27. King, A. M. Q., F. Brown, P. Christian, T. Hovi, T. Hyypia, N. J. Knowles, S. M. Lemon, P. D. Minor, A. C. Palmenberg, T. Skern, and G. Stanway. 2000. Picornaviridae, p. 657-678. In M. H. V. van Regenmortel, C. M. Fauquet, D. H. L. Bishop, E. B. Carstens, M. K. Estes, S. M. Lemon, J. Maniloff, M. A. Mayo, D. J. McGeoch, C. R. Pringle, and R. B. Wickner (ed.), Virus Taxonomy. Seventh Report of the International Committee for the Taxonomy of Viruses. Academic Press, San Diego, Calif.
28. Kling, S., H. Donninger, Z. Williams, J. Vermeulen, E. Weinberg, K. Latiff, R. Ghildyal, and P. Bardin. 2005. Persistence of rhinovirus RNA after asthma exacerbation in children. *Clin. Exp. Allergy.* 35:672-678.
29. Lamson, D., N. Renwick, V. Kapoor, Z. Liu, G. Palacios, J. Ju, A. Dean, K. St George, T. Briese, and W. I. Lipkin. 2006. MassTag polymerase-chain-reaction detection of respiratory pathogens, including a new rhinovirus genotype that caused influenza-like illness in New York State during 2004-2005. *J. Infect. Dis.* 194:1398-1402.
30. Ledford, R. M., N. R. Patel, T. M. Demenczuk, A. Watanyar, T. Herbertz, M. S. Collett, and D. C. Pevear. 2004. VP1 sequencing of all human rhinovirus serotypes: insights into genus phylogeny and susceptibility to antiviral capsid-binding compounds. *J. Virol.* 78:3663-3674.
31. Loens, K., H. Goossens, C. de Laat, H. Foolen, P. Oudshoorn, S. Pattyn, P. Sillekens, and M. Ieven. 2006. Detection of rhinoviruses by tissue culture and two independent amplification techniques, nucleic acid sequence-based amplification and reverse transcription-PCR, in 31. children with acute respiratory infections during a winter season. *J. Clin. Microbiol.* 44:166-171.
32. Lu, X., M. Chittaganpitch, S. J. Olsen, I. M. Mackay, T. P. Sloots, A. M. Fry, and D. D. Erdman. 2006. Real-time PCR assays for detection of bocavirus in human specimens. *J. Clin. Microbiol.* 44:3231-3235.
33. McErlean, P., L. A. Shackelton, S. B. Lambert, M. D. Nissen, T. P. Sloots, and I. M. Mackay. 2007. Characterisation of a newly identified human rhinovirus, HRV-QPM, discovered in infants with bronchiolitis. *J. Clin. Virol.* 39:67-75.
34. Miller, E. K., X. Lu, D. D. Erdman, K. A. Poehling, Y. Zhu, M. R. Griffin, T. V. Hartert, L. J. Anderson, G. A. Weinberg, C. B. Hall, M. K. Iwane, K. M. Edwards, and New Vaccine Surveillance Network. 2007. Rhinovirus-associated hospitalizations in young children. *J. Infect. Dis.* 195:773-781.
35. Monto, A. S., A. M. Fendrick, and M. W. Sarnes. 2001. Respiratory illness caused by picornavirus infection: a review of clinical outcomes. *Clin. Ther.* 23:1615-1627.
36. Nicholson, K. G., J. Kent, V. Hammersley, and E. Cancio. 1996. Risk factors for lower respiratory complications of rhinovirus infections in elderly people living in the community: prospective cohort study. *Br. Med. J.* 313:1119-1123.
37. Nielsen, C. B., S. K. Singh, J. Wengel, and J. P. Jacobsen. 1999. The solution structure of a locked nucleic acid (LNA) hybridized to DNA. *J. Biomol. Struct. Dyn.* 17:175-191.
38. Nijhuis, M., N. van Maarseveen, R. Schuurman, S. Verkuijlen, M. de Vos, K. Hendriksen, and A. M. van Loon. 2002. Rapid and sensitive routine detection of all members of the genus enterovirus in different clinical specimens by real-time PCR. *J. Clin. Microbiol.* 40:3666-3670.
39. Nokso-Koivisto, J., T. J. Kinnari, P. Lindahl, T. Hovi, and A. Pitkäranta. 2002. Human picornavirus and coronavirus RNA in nasopharynx of children without concurrent respiratory symptoms. *J. Med. Virol.* 66:417-420.
40. Pallansch, M. A., and R. P. Roos. 2001. Enteroviruses: polioviruses, coxsackieviruses, echoviruses, and newer enteroviruses. p. 723-775. In D. M. Knipe, P. M. Howley, D. E. Griffin, R. A. Lamb, M. A. Martin, B. Roizman, and S. E. Straus (ed.), Fields Virology. Philadelphia, Pa.
41. Papadopoulos, N. G., J. Hunter, G. Sanderson, J. Meyer, and S. L. Johnston. 1999. Rhinovirus identification by BglI digestion of picornavirus RT-PCR amplicons. *J. Virol. Methods.* 80:179-85.
42. Pitkaranta, A., and F. G. Hayden. 1998. Rhinoviruses: important respiratory pathogens. *Ann. Med.* 30:529-537.
43. Savolainen, C., S. Blomqvist, M. N. Mulders, and T. Hovi 2002. Genetic clustering of all 102 human rhinovirus prototype strains: serotype 87 is close to human enterovirus 70. *J. Gen. Virol.* 83:333-340.
44. Scheltinga, S. A., K. E. Templeton, M. F. Beersma, and E. C. Claas. 2005. Diagnosis of human metapneumovirus and rhinovirus in patients with respiratory tract infections by an internally controlled multiplex real-time RNA PCR. *J. Clin. Virol.* 33:306-311.
45. Schrag, S. J., J. T. Brooks, C. Van Beneden, U. D. Parashar, P. M. Griffin, L. J. Anderson, W. J. Bellini, R. F. Benson, D. D. Erdman, A. Klimov, T. G. Ksiazek, T. C. Peret, D. F. Talkington, W. L. Thacker, M. L. Tondella, J. S. Sampson, A. W. Hightower, D. F. Nordenberg, B. D. Plikaytis, A. S. Khan, N. E. Rosenstein, T. A. Treadwell, C. G. Whitney, A. E. Fiore, T. M. Durant, J. F. Perz, A. Wasley, D. Feikin, J. L. Herndon, W. A. Bower, B. W. Klibourn, D. A. Levy, V. G. Coronado, J. Buffington, C. A. Dykewicz, R. F. Khabbaz, and M. E. Chamberland. 2004. SARS surveillance during emergency public health response, United States, March-July 2003. *Emerg. Infect. Dis.* 10:185-194.
46. Smyth, A. R., R. L. Smyth, C. Y. Tong, C. A. Hart, and D. P. Heaf. 1995. Effect of respiratory virus infections including rhinovirus on clinical status in cystic fibrosis. *Arch. Dis. Child.* 73:117-120.
47. Verstrepen, W. A., S. Kuhn, M. M. Kockx, M. E. Van De Vyvere, and A. H. Mertens. 2001. Rapid detection of enterovirus RNA in cerebrospinal fluid specimens with a novel single-tube real-time reverse transcription-PCR assay. *J. Clin. Microbiol.* 39:4093-4096.
48. Wald, T., P. Shult, P. Krause, B. Miller, P. Drinka, and S. Gravenstein. 1995. A rhinovirus outbreak among residents of a long-term care facility. *Ann. Intern. Med.* 123:588-593.
49. Wittwer, C. T., M. G. Herrmann, A. A. Moss, and R. P. Rasmussen. 1997. Continuous fluorescence monitoring of rapid cycle DNA amplification. *Biotechniques* 22:130-131, 134-138.
50. Witwer, C., S. Rauscher, I. L. Hofacker, and P. F. Stadler. 2001. Conserved RNA secondary structures in Picornaviridae genomes. *Nucleic Acids Res.* 29:5079-5089.
51. Wright, P. F., A. M. Deatly, R. A. Karron, R. B. Belshe, J. R. Shi, W. C. Gruber, Y. Zhu, and V. B. Randolph. 2007. Comparison of results of detection of rhinovirus by PCR and viral culture in human nasal wash specimens from subjects with and without clinical symptoms of respiratory illness. *J. Clin. Microbiol,* 45:2126-2129.
52. Allander, T., M. Tammi, M. Eriksson, A. Bjerkner, A. Tiveljung-Lindell, and B. Andersson. 2005. Cloning of a human parvovirus by molecular screening of respiratory tract samples. *PNAS* 102:12891-12896.
53. Bastien, N., K. Brandt, K. Dust, D. Ward, and Y. Li. 2006. Human bocavirus infection, Canada. *Emerg. Infect. Dis.* 12:848-850.
54. Bustin, S. A., and T. Nolan. 2004. A-Z of quantitative PCR. International University Line, La Jolla, Calif.
55. Chenna, R., H. Sugawara, T. Koike, R. Lopez, T. J. Gibson, D. G. Higgins, and J. D. Thompson. 2003. Multiple sequence alignment with the Clustal series of programs. Nucleic Acids Res. 31:3497-3500.
56. Emery, S. L., D. D. Erdman, M. D. Bowen, B. R. Newton, J. M. Winchell, R. F. Meyer, S. Tong, B. T. Cook, B. P. Holloway, K. A. McCaustland, P. A. Rota, B. Bankamp, L. E. Lowe, T. G. Ksiazek, W. J. Bellini, and L. J. Anderson. 2004. Real-time reverse transcription-polymerase chain reaction assay for SARS-associated coronavirus. *Emerg. Infect. Dis.* 10:311-316.
57. Foulongne, V., M. Rodiere, and M. Segondy. 2006. Human bocavirus in children. *Emerg. Infect. Dis.* 12:862-863.
58. Ma, X., R. Endo, N. Ishiguro, T. Ebihara, H. Ishiko, T. Ariga, and H. Kikuta. 2006. Detection of human bocavirus in Japanese children with lower respiratory tract infections. *J. Clin. Microbiol.* 44:1132-1134.
59. Sloots, T. P., P. McErlean, D. J. Speicher, K. E. Arden, M. D. Nissen, and I. M. Mackay. 2006. Evidence of human coronavirus HKU1 and human bocavirus in Australian children. *J. Clin. Virol.* 35:99-102.
60. Tattersall, P. 2005. Family Parvoviridae, p. 353-369. In C. M. Fauquet, M. A. Mayo, J. Maniloff, U. Desselberger, and L. A. Ball (ed.), Virus taxonomy: classification and nomenclature of viruses. Eighth report of the International Committee on the Taxonomy of Viruses. Elsevier Academic Press, London, United Kingdom.
61. Xiaoyan Lu, Malinee Chittaganpitch, Sonja J. Olsen, Ian M. Mackay, Theo P. Sloots, Alicia M. Fry, and Dean D. Erdman. 2006. Real-Time PCR Assays for Detection of Bocavirus in Human Specimens. *J Clin. Microbiol., Vol.* 44, p. 3231-3235.
62. Lawrence B. Blyn, Thomas A. Hall, Brian Libby, Raymond Ranken, Rangarajan Sampath, Karl Rudnick, Emily Moradi, Anjali Desai, David Metzgar, Kevin L. Russell, Nikki E. Freed, Melinda Balansay, Michael P. Broderick, Miguel A. Osuna, Steven A. Hofstadler, and David J. Ecker 2008. Rapid Detection and Molecular Serotyping of Adenovirus by Use of PCR Followed by Electrospray Ionization Mass Spectrometry *J. Clin. Microbiol.* 46: 644-651.
63. Jiang Y, Hofstadler S A. 2003. A highly efficient and automated method of purifying and desalting PCR products for analysis by electrospray ionization mass spectrometry. *Anal. Biochem.* 316: 50-57.
64. Karlin and Altschul, 1990, *PNAS* 87:2264 2268.
65. Karlin and Altschul, 1993, *PNAS* 90:5873 5877.
66. Altschul et al., 1990, *J. Mol. Biol.* 215:403.
67. Altschul et al., 1997, *Nucleic Acids Res.* 25:3389 3402.
68. Myers and Miller, 1988, *CABIOS* 4:11 17.
69. Holland et al., *PNAS* 88(16):7276 (1991).
70. Saiki et al., *BioTechnology* 3:1008 1012 (1985).
71. Conner et al., *PNAS* 80: 278 (1983).
72. Landegren et al., *Science* 241:1077 (1988).
73. Ortiz, A and Ritter, E, *Nucleic Acids Res.,* 1996; 24:3280-3281.
74. Lishanski, A, et al., *Nucleic Acids Res.,* 2000; 28(9):e42.
75. Lee, K., *Biotechnology Letters,* 2003; 25:1739-1742.
76. Johnson, *Annual Reviews of Biochemistry,* 1993: 62:685-713.
77. Kunkel, *Journal of Biological Chemistry,* 1992; 267: 18251-18254.

The invention claimed is:

1. A process of detecting human rhinovirus in a biological sample comprising: producing an amplification product by amplifying a human rhinovirus nucleotide sequence using forward primers consisting of the sequence of SEQ ID NO: 1 and homologous to a region within nucleotides 356-563 of human rhinovirus, and a reverse primer consisting of the sequence of SEQ ID NO: 2 and homologous to a region within nucleotides 356-563 of human rhinovirus, under conditions suitable for a polymerase chain reaction; and measuring said amplification product to detect human rhinovirus in said biological sample, wherein the step of measuring is by hybridizing a probe to said amplification product and detecting a first detection signal from said probe hybridized to said amplification product.

2. The process of claim 1 wherein said measuring comprises hybridizing probes of SEQ ID NO: 3 to said amplification product.

3. The process of claim 1 wherein said detecting diagnoses human rhinovirus infection.

4. The process of claim 1 further comprising comparing said first detection signal to a second detection signal, wherein said second detection signal results from detection of a second amplification product produced from a sequence of a virus selected from the group comprising human enterovirus, polio virus, respiratory syncytial virus, human metapneumovirus, human parainfluenza viruses 1-4, adenovirus, coronaviruses 229E and OC43, influenza viruses A and B, and human bocavirus, and the hybridization of a probe complementary to a sequence from one or more viruses of said group.

5. The process of claim 1 further comprising comparing said first detection signal to a second detection signal, wherein said second detection signal results from detection of a second amplification product produced from a control sequence of human rhinovirus using a forward primer homologous to a region within nucleotides 356-563 of human rhinovirus, and a reverse primer homologous to a region within nucleotides 356-563 of human rhinovirus, and the hybridization of a probe complementary to a sequence from human rhinovirus.

6. The process of claim 5 wherein said second detection signal is generated in parallel with said first detection signal.

7. The process of claim 5, wherein said second amplification product is generated by PCR amplification of a human rhinovirus target sequence.

8. The process of claim 5, wherein said first detection signal is compared to a third detection signal from a nucleic acid calibrator extracted in parallel to said biological sample.

9. The process of claim 8, wherein said nucleic acid calibrator comprises a known amount of human rhinovirus and a known amount of a medium similar to the biological sample.

* * * * *

SEQUENCE LISTING

```
<160> NUMBER OF SEQ ID NOS: 14

<210> SEQ ID NO 1
<211> LENGTH: 14
<212> TYPE: DNA
<213> ORGANISM: Artificial Sequence
<220> FEATURE:
<223> OTHER INFORMATION: Forward primer for human rhinovirus detection
<220> FEATURE:
<221> NAME/KEY: misc_feature
<222> LOCATION: (2)..(2)
<223> OTHER INFORMATION: n is a pyrimidine derivative base that mimics
      function of C or T
<220> FEATURE:
<221> NAME/KEY: misc_feature
<222> LOCATION: (3)..(3)
<223> OTHER INFORMATION: n is a locked nucleic acid (LNA) deoxyadenosine
      LNA-dA
<220> FEATURE:
<221> NAME/KEY: misc_feature
<222> LOCATION: (7)..(7)
<223> OTHER INFORMATION: n is a locked nucleic acid (LNA) deoxyadeosine
      LNA-dT
<220> FEATURE:
<221> NAME/KEY: misc_feature
<222> LOCATION: (14)..(14)
<223> OTHER INFORMATION: y is a base of C or T

<400> SEQUENCE: 1
cnngccngcg tggy                                                          14

<210> SEQ ID NO 2
<211> LENGTH: 21
<212> TYPE: DNA
<213> ORGANISM: Artificial Sequence
<220> FEATURE:
<223> OTHER INFORMATION: Reverse primer for residue 563-593 of HRV1B
      (Accession No. D00239)

<400> SEQUENCE: 2
gaaacacgga cacccaaagt a                                                  21

<210> SEQ ID NO 3
<211> LENGTH: 22
<212> TYPE: DNA
<213> ORGANISM: Artificial Sequence
<220> FEATURE:
<223> OTHER INFORMATION: Nucleic acid probe for human rhinovirus
```

```
<220> FEATURE:
<221> NAME/KEY: misc_feature
<222> LOCATION: (19)..(19)
<223> OTHER INFORMATION: y is a base of C or T

<400> SEQUENCE: 3
tcctccggcc cctgaatgyg gc                                                22

<210> SEQ ID NO 4
<211> LENGTH: 32
<212> TYPE: DNA
<213> ORGANISM: Artificial Sequence
<220> FEATURE:
<223> OTHER INFORMATION: Forward primer for human rhinovirus A NCR
      sequencings
<220> FEATURE:
<221> NAME/KEY: misc_feature
<222> LOCATION: (26)..(26)
<223> OTHER INFORMATION: y is a base of C or T
<220> FEATURE:
<221> NAME/KEY: misc_feature
<222> LOCATION: (28)..(28)
<223> OTHER INFORMATION: y is a base of C or T

<400> SEQUENCE: 4
gtactctgtt attccggtaa ctttgyaygc ca                                     32

<210> SEQ ID NO 5
<211> LENGTH: 32
<212> TYPE: DNA
<213> ORGANISM: Artificial Sequence
<220> FEATURE:
<223> OTHER INFORMATION: Reverse primer for human rhinovirus A NCR
      sequencings
<220> FEATURE:
<221> NAME/KEY: misc_feature
<222> LOCATION: (21)..(21)
<223> OTHER INFORMATION: y is a base of C or T
<220> FEATURE:
<221> NAME/KEY: misc_feature
<222> LOCATION: (24)..(24)
<223> OTHER INFORMATION: d is a deoxy-a, deoxy-t or deoxy-g
<220> FEATURE:
<221> NAME/KEY: misc_feature
<222> LOCATION: (27)..(27)
<223> OTHER INFORMATION: v is deoxy-a, deoxy-c or deoxy-g

<400> SEQUENCE: 5
ccaacattct gtctagatac ytgdgcvccc at                                     32

<210> SEQ ID NO 6
<211> LENGTH: 32
<212> TYPE: DNA
<213> ORGANISM: Artificial Sequence
<220> FEATURE:
<223> OTHER INFORMATION: Forward primer for human rhinovirus B NCR
      sequencings

<400> SEQUENCE: 6
actctggtac tatgtacctt tgtacgcctg tt                                     32

<210> SEQ ID NO 7
<211> LENGTH: 32
<212> TYPE: DNA
<213> ORGANISM: Artificial Sequence
<220> FEATURE:
<223> OTHER INFORMATION: Forward primer for human rhinovirus B NCR
      sequencings
```

```
<220> FEATURE:
<221> NAME/KEY: misc_feature
<222> LOCATION: (21)..(21)
<223> OTHER INFORMATION: y is a base of C or T
<220> FEATURE:
<221> NAME/KEY: misc_feature
<222> LOCATION: (24)..(24)
<223> OTHER INFORMATION: d is deoxy-a, deoxy-t or deoxy-g
<220> FEATURE:
<221> NAME/KEY: misc_feature
<222> LOCATION: (27)..(27)
<223> OTHER INFORMATION: d is deoxy-a, deoxy-t or deoxy-g

<400> SEQUENCE: 7
ccactcttct gtgtagacac ytgdgcdccc at                              32

<210> SEQ ID NO 8
<211> LENGTH: 35
<212> TYPE: DNA
<213> ORGANISM: Artificial Sequence
<220> FEATURE:
<223> OTHER INFORMATION: Forward primer for human rhinovirus 14 RNA
      transcription

<400> SEQUENCE: 8
taatacgact cactataggg caagcacttc tgttt                           35

<210> SEQ ID NO 9
<211> LENGTH: 36
<212> TYPE: DNA
<213> ORGANISM: Artificial Sequence
<220> FEATURE:
<223> OTHER INFORMATION: Reverse primer for human rhinovirus 14 RNA
      transcription

<400> SEQUENCE: 9
atttaggtga cactatagaa gcatctggta atttcc                          36

<210> SEQ ID NO 10
<211> LENGTH: 37
<212> TYPE: DNA
<213> ORGANISM: Artificial Sequence
<220> FEATURE:
<223> OTHER INFORMATION: Forward primer for human enterovirus 68 RNA
      transcription

<400> SEQUENCE: 10
taatacgact cactataggg tcttatgagc aagcact                         37

<210> SEQ ID NO 11
<211> LENGTH: 40
<212> TYPE: DNA
<213> ORGANISM: Artificial Sequence
<220> FEATURE:
<223> OTHER INFORMATION: Reverse primer for human enterovirus 68 RNA
      transcription

<400> SEQUENCE: 11
atttaggtga cactatagaa attacttcaa ataaactcag                      40

<210> SEQ ID NO 12
<211> LENGTH: 14
<212> TYPE: DNA
<213> ORGANISM: Artificial Sequence
<220> FEATURE:
<223> OTHER INFORMATION: Consensus Sequence
```

```
<400> SEQUENCE: 12
ctagcctgcg tggc                                                        14

<210> SEQ ID NO 13
<211> LENGTH: 22
<212> TYPE: DNA
<213> ORGANISM: Artificial Sequence
<220> FEATURE:
<223> OTHER INFORMATION: Consensus Sequence

<400> SEQUENCE: 13
tcctccggcc cctgaatgcg gc                                               22

<210> SEQ ID NO 14
<211> LENGTH: 21
<212> TYPE: DNA
<213> ORGANISM: Artificial Sequence
<220> FEATURE:
<223> OTHER INFORMATION: Consensus Sequence

<400> SEQUENCE: 14
tactttgggt gtccgtgttt c                                                21
```